United States Patent [19]

Pohto et al.

[11] Patent Number: 5,288,750
[45] Date of Patent: * Feb. 22, 1994

[54] SUBSTITUTED β-DIKETONES

[75] Inventors: Pentti Pohto; Päivi A. Aho; Reijo J. Bäckström, all of Helsinki; Erkki J. Honkanen, Vantaa; Inge-Britt Y. Linden, Helsinki; Erkki A. O. Nissinen, Espoo, all of Finland

[73] Assignee: Orion-yhtymä Oy, Espoo, Finland

[*] Notice: The portion of the term of this patent subsequent to Feb. 9, 2010 has been disclaimed.

[21] Appl. No.: 646,714

[22] PCT Filed: Sep. 1, 1989

[86] PCT No.: PCT/FI89/00165
§ 371 Date: Jan. 31, 1991
§ 102(e) Date: Jan. 31, 1991

[87] PCT Pub. No.: WO90/02724
PCT Pub. Date: Mar. 22, 1990

[30] Foreign Application Priority Data

Sep. 1, 1988 [GB] United Kingdom ............... 8820729

[51] Int. Cl.⁵ .............. A61K 31/38; A61K 3/12; C07C 49/794; C07D 333/22
[52] U.S. Cl. .................. 514/438; 514/311; 514/354; 514/356; 514/441; 514/445; 514/447; 514/461; 514/471; 514/472; 514/473; 514/520; 514/544; 514/543; 514/547; 514/569; 514/570; 514/672; 514/675; 514/678; 514/688; 546/174; 546/340; 546/341; 546/342; 549/60; 549/64; 549/66; 549/68; 549/69; 549/78; 549/479; 549/480; 549/498; 558/414; 560/80; 560/82; 560/191; 560/192; 560/195; 560/196; 560/197; 560/201; 562/459; 562/462; 562/464; 562/465
[58] Field of Search .............. 549/60, 64, 66, 68, 549/69, 78, 479, 480; 558/414; 568/306, 307, 308, 328, 313, 336, 337, 412, 413; 562/462, 463, 464, 459; 560/192, 193, 191, 196, 197, 201; 514/448, 445, 447, 438, 471, 472, 473, 461, 520, 675, 677, 678, 688, 569, 570, 547, 549, 543

[56] References Cited

U.S. PATENT DOCUMENTS 3,280,069 10/1966 Knapp et al. .................. 260/45.85

(List continued on next page.)

FOREIGN PATENT DOCUMENTS 612352 9/1988 Australia .

(List continued on next page.)

OTHER PUBLICATIONS

D. Vegh, *Collection of Czechoslovak Chem. Commun.,* 50, pp. 1415-1421 (1985).

(List continued on next page.)

*Primary Examiner*—Richard L. Raymond
*Attorney, Agent, or Firm*—Burns, Doane, Swecker & Mathis

[57] ABSTRACT

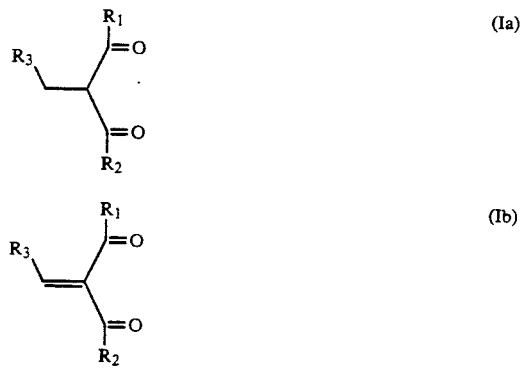

wherein $R_1$ and $R_2$ are each independently hydrogen, alkyl of 1 to 6 carbon atoms, alkoxy of 1 to 6 carbon atoms, hydroxy, aryl or heteroaryl or amino, the alkyl, aryl, heteroaryl or amino group being optionally substituted; $R_3$ is hydrogen, optionally substituted alkyl of 1 to 6 carbon atoms or optionally substituted aryl or heteroaryl and salts, ethers and esters thereof are useful as cytoprotective agents, especially as antiulcerogenic or gastroprotective agents.

10 Claims, No Drawings

U.S. PATENT DOCUMENTS

| | | | |
|---|---|---|---|
| 3,856,911 | 12/1974 | Yokotani et al. | 514/678 |
| 3,860,598 | 1/1975 | Rosenkranz et al. | 546/174 |
| 3,998,872 | 12/1976 | Symon et al. | 260/483 |
| 4,153,719 | 5/1979 | Diana | 424/286 |
| 4,456,770 | 6/1984 | Everly et al. | 568/315 |
| 5,001,152 | 3/1991 | Aho et al. | 558/412 |
| 5,112,861 | 5/1992 | Backstrom et al. | 514/520 |
| 5,185,370 | 2/1993 | Backstrom et al. | 514/520 |

FOREIGN PATENT DOCUMENTS

| | | |
|---|---|---|
| 622195 | 7/1989 | Australia . |
| 0008458 | 3/1980 | European Pat. Off. . |
| 0052300 | 5/1982 | European Pat. Off. . |
| 0308785 | 3/1989 | European Pat. Off. . |
| 0323162 | 7/1989 | European Pat. Off. . |
| 2155495 | 11/1971 | Fed. Rep. of Germany . |
| 2210633 | 9/1973 | Fed. Rep. of Germany . |
| 3303066 | 12/1984 | Fed. Rep. of Germany . |
| 2607493 | 6/1988 | France . |
| WO90/02724 | 3/1990 | PCT Int'l Appl. . |
| 629741 | 1/1978 | Switzerland . |
| 2200109 | 7/1988 | United Kingdom . |

OTHER PUBLICATIONS

E. Solconiova et al., *Chemical Abstracts*, 96:198944j, p. 603, (1982), abstract of *Org. Magn. Reson.*, 1982, 18(1), 55-7.

M. Jiang et al., *Chemical Abstracts*, 108:149798x, p. 670, (1988), abstract of *Jiegou Huaxue*, 1986, 5(4), 221-30.

S. Marchalin et al., *Chemical Abstracts*, 109:149244j, p. 706, (1988), abstract of *Z. Chem.*, 1987, 27(11), 406-7.

Yamashita et al., *Tetrahydron Letters*, No. 22 and 23, pp. 1867-1868 (1975).

E. Pohjala et al., *Chemical Abstracts*, 96:217042g, p. 667, (1982), abstract of *Org. Mass Spectrom*, 1981, 16(12) 519-22.

A. Rosado et al., *Chemical Abstracts*, 93:185229t, p. 565, (1980) abstract of *Rev. CENIC, Cienc Fis.*, 1977, 8(1), 1-13.

M. Go et al., *Chemical Abstracts*, 101:90689n, p. 619, (1984), abstract of *Acta Pharm. Science*, 1984 21(1), 77-80.

G. Papagan et al., *Chemical Abstracts*, 74:12913r, pp. 290-291, (1971), abstract of *Aim. Khim Zh.*, 1970, 23(6), 542-9.

G. Holmberg et al., *Chemical Abstracts*, 82:43111v, pp. 412-413, (1975), abstract of *Acta Chem. Scand., Ser. B*, 1974, 28(8), 909-912.

Vegh, *Chemical Abstracts*, 109:211082k, p. 669, (1988), abstract of Czech. CS 245,801, Dec. 15, 1987.

J. Dimmock et al., *Chemical Abstracts*, 110:94935y, pp. 667, (1989), abstract of *Eur. J. Med. Chem.*, 1988 23(2) 111-17.

W. Lehnut, *Chemical Abstracts*, 81:169036d, p. 506, (1974), abstract of *Synthesis*, (9) 667-669 (1974).

M. Manroa et al., *Chemical Abstracts*, 101:85528e, p. 205, (1984), abstract of *Pesticides*, 1984 18(2) 30,36.

Toshio Kawata et al., *Bulletin of the Chemical Society of Japan*, vol. 48(3), 1975, "The Chelation of 3-(p-Hydroxybenzylidene-2,4-pentanedione with the Thallous Ion"; pp. 882-884.

Masaaki Iwata et al., *Bulletin of the Chemical Society of Japan*, vol. 49(5), 1976, "Aldol Condensation of Aldehydes with Ketones Promoted by the Cooper (II) Ion. Orientation to the Chemical Model for Metalloaldolases"; pp. 1369-1374.

Jean-Paul Vecchionacci et al., *Bulletin Societe Chiminique de France*, vol. 7-8, 1974, "Réactions de Friedel et Crafts du benzéne, de l'anisole et du méta-diméthoxybenzéne sur des styrénes β,β-disubstitués par des groupements électroattracteurs"; pp. 1683-1690.

Jonathan R. Dimmock et al., *Eur. Journal of Med. Chem.*, vol. 23, No. 2, 1988, "Evaluation of Mannich bases of 2-arylidene-1,3-diketones versus murine P388 leukemia"; pp. 111-117.

Ikuo Katsumi et al., *Chem. Pharm. Bulletin*, vol. 34, No. 4, 1986, "Studies on Styrene Derivatives. II. Synthesis and Antiinflammatory Activity of 3,5-Di-tert-butyl-4-hydroxystyrenes"; pp. 1619-1627.

SUBSTITUTED β-DIKETONES

The present invention relates to β-diketones and their physiologically acceptable salts, ester and ethers, and pharmaceutical compositions containing these compounds which are useful as cytoprotective agents and in particular as antiulcerogenic or gastroprotective agents.

Finnish patent application No. 864875 discloses a group of compounds including the β-ketone 3-(3,4-dihydroxy-5-tri-fluoromethylbenzylidene)-2,4-pentanedione, which have been shown to be effective medicoments for treating for instance, Parkinsonism.

British patent application No. 8730190 discloses a group of compounds including the β-diketone 3-(3,4-dihydroxy-5-nitrobenzylidene)-2,4-pentanedione, and European patent application No. 88312228.5 discloses a group of compounds including the β-ketones 3-(3-hydroxy-4-methoxy-5-nitro-benzylidene)-2,4-pentanedione, 3-(4-hydrox nitrobenzylidene)-2,4-pentanedione, 3-(3-chloro-5-ethoxy-4-hydroxybenzylidene)-2,4-pentanedione and 3-(3-chloro-4,5-dihydroxybenzylidene)-2,4-pentanedione. These compo are useful as agents for the treatment or prophylaxis of ulcers, lesions or like condition in the gastrointestinal tract. It has now been found that other β-diketones are effective as cytoprotective agents, and in particular are useful in the treatment or prophylaxis of ulcers, lesions or like condition in the gastrointestinal tract.

The present invention provides a compound of the formula Ia or Ib

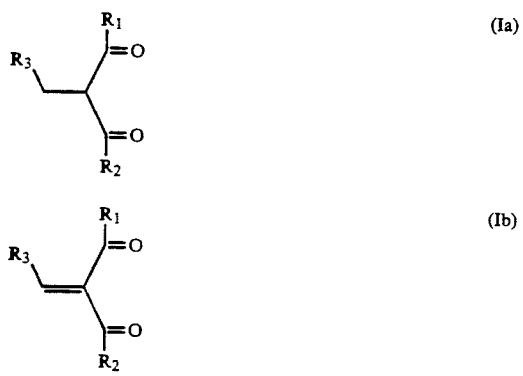

wherein $R_1$ and $R_2$ are each independently hydrogen, $C_{1-6}$ alkyl, $C_{1-6}$ alkoxy, hydroxy, aryl or heteroaryl, or amino, the alkyl, aryl, heteroaryl or amino group being optionally substituted;

$R_3$ is hydrogen, optionally substituted $C_{1-6}$ alkyl, or optionally substituted aryl or heteroaryl, or a salt, ether or ester thereof, provided that the compound of formula Ib is not 3-(3,4-dihydroxy-5-trifluoromethylbenzylidene)-2,4-pentanedione, 3-(3,4-dihydroxy-5-nitrobenzylidene)-2,4-pentanedione, 3(3-hydroxy-4-methoxy-5-nitrobenzylidene)-2,4-pentanedione, 3-(4-hydroxy-3-methoxy-5-nitrobenzylidene)-2,4-pentanedione, 3-(3-chloro-5-ethoxy-4-hydroxybenzylidene)-2,4-pentanedione or 3-(3-chloro-4,5-dihydroxybenzylidene)-2,4-pentanedione.

Preferably the optional substituent on the amino is an alkyl of 1 to 6 carbon atoms or an aryl group.

Preferably the optional substituent on an alkyl group is hydroxy, alkoxy of 1 to 6 carbon atoms, halogens, nitro or amino, and the alkyl group does not carry more than three substituents.

Preferably the aryl group is phenyl or naphthyl which may be substituted by alkyl of 1 to 6 carbon atoms, hydroxy, alkoxy of 1 to 6 carbon atoms, trifluoromethyl, cyano, amino or carboxy or a diketo which is attached to the aryl group either directly or via a saturated hydrocarbon of 1 to 3 carbon atoms or an unsaturated hydrocarbon of two or three carbon atoms. The number of optional substituents on the aryl group is preferably 1 to 3 and the substituents may be the same or different.

Preferably the heteroaryl group is pyridyl, quinolyl, thienyl or furyl which is optionally substituted by an alkyl of one to six carbon atoms, hydroxy, alkoxy of one to six carbon atoms, halogen, nitro or amino. The number of optional substituents on the heteroaryl group is preferably 1 or 2 and the substituents may be the same or different.

Particularly preferred compounds of the invention are those of formula Ib since the carbon carbon double bond forms a conjugated system of double bonds with the keto groups.

Preferred compounds also include those in which $R_1$ and $R_2$ are each $C_{1-4}$ alkyl and $R_3$ is thienyl, furyl, or phenyl which is substituted by hydroxy, $C_{1-4}$ alkoxy, trifluoromethyl or cyano, or $R_3$ is carboxyphenyl.

The present invention also provides a compound of formula Ia or Ib as defined above for use as a cytoprotective agent, provided that the compound of formula Ib is not 3-(3,4-dihydroxy-5-trifluoromethylbenzylidene)-2,4-pentanedione, 3-(3,4-dihydroxy-5-nitrobenzylidene)-2,4-pentanedione, 3(3-hydroxy-4-methoxy-5-nitrobenzylidene)-2,4-pentanedione, 3-(4-hydroxy-3-methoxy-5-nitrobenzylidene)-2,4-pentanedione, 3-(3-chloro-5-ethoxy-4-hydroxybenzylidene)-2,4-pentanedione or 3-(3-chloro-4,5-dihydroxybenzylidene)-2,4-pentanedione.

The present invention further provides a compound of formula Ia or Ib as defined above for use in the manufacture of a medicament for the treatment or prophylaxis of ulcers, lesions or like conditions in the gastrointestinal tract, provided that the compound of formula Ib is not 3-(3,4-dihydroxy-5-nitrobenzylidene)-2,4-pentanedione, 3-(3-hydroxy-4-methoxy-5-nitrobenzylidene)-2,4-pentanedione, 3-4-hydroxy 3-methoxy-5-nitrobenzylidene)-2,4-pentanedione, 3-(3-chloro-5-ethoxy-4-hydroxybenzylidene)-2,4-pentanedione or 3-(3-chloro-4,5-dihydroxybenzylidene)-2,4-pentanedione.

Preferable salts of compounds of formula Ia and Ib are those formed with sodium, potassium, ammonium, calcium, magnesium or organic bases. Preferred esters and ethers are acyl or aroyl derivatives which will hydrolyse under physiological conditions.

The compounds of formula I (a),(b) may be prepared by reacting a compound of formula II $$R_1\text{—CO—CH}_2\text{—CO—}R_2 \qquad \text{II}$$

in which $R_1$ and $R_2$ are as defined above with a compound of formula III $$R_3\text{—Z} \qquad \text{III}$$

in which $R_3$ is as defined above and Z is CHO or —CH$_2$—Q, wherein Q is halogen or some other activated group, in the presence of acid or base catalyst to produce the compounds of formula I (a) and (b), whereafter, if needed, the compound according to formula Ia is halogenated to give a compound of the formula IV

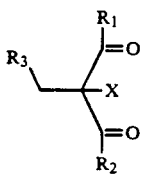

in which $R_1$, $R_2$ and $R_3$ are as defined above and x is halogen and dehydrohalogenating compound IV to produce compounds of the formula Ib, and if needed compounds according to formula Ib may be reduced to give compounds of the formula Ia.

The basic catalyst may be for example an inorganic base or an organic amine. The acid catalyst may be for example a mineral acid or sulfonic acid. The activated group Q may be a halogen or an alkyl or aryl sulphonate.

When halogenating a compound of formula Ia elementary halogen, preferably chlorine or bromine may be used, or another known balogenating agent such as sulfuryl chloride may be used.

The present invention provides a pharmaceutical composition comprising a compound of formula Ia or Ib as defined above or a salt, ether or ester thereof, and a pharmaceutically acceptable carrier or diluent.

The composition may be for example in the form of a tablet, dragee, capsule, suppository, emulsion, suspension or solution. It may contain a pharmaceutically acceptable additive or excipient such as a solvent, gel or dispersion forming agent, an antioxidant or a colorant.

The effective dose varies depending on whether the compounds are given for prophylaxis or for treatment of a condition which is already present. The daily dose and number of doses are dependent on the severity of the condition to be treated. The effective dose is generally from about 1 to 1000 mg of compound per day, preferably typically 100 to 600 mg per day. The following examples illustrate the invention.

EXAMPLE 1

3-(4-Carboxybenzylidene)-2,4-pentanedione

To a suspension containing 3.0 g (0.02mol) of 4-carboxybenzaldehyde and 3.0 g (0.03mol) of 2,4-pentanedione in 10ml of 2-propanol was gradually added 3.0 g (0.025mol) of thionyl chloride with stirring and cooling (below 20° C). The mixture was stirred over night at 20° C. After filtering the product was washed with 2-propanol, yield 1.8 g, mp 195°–199° C.

EXAMPLE 2

3-(4-Hydroxybenzylidene)-2,4-pentanedione

The procedure described in example 1 was repeated by using 4-hydroxybenzaldehyde instead of 4-carboxybenzaldehyde. Mp 123°–127° C.

EXAMPLE 3

3-(4-methoxybenzylidene)-2,4-pentanedione

The procedure described in example 1 was repeated by using 4-methoxybenzaldehyde instead of 4-carboxybenzaldehyde. Mp 70°–72° C.

EXAMPLE 4

3-(Benzylidene)-2,4-pentanedione

The procedure described in example 1 was repeated by using benzaldehyde instead of 4-carboxybenzaldehyde. Colorless oil, bp 186°–188° C/16 mm.

EXAMPLE 5

3-Ethylidene-2,4-pentanedione

The procedure described in example 1 was repeated by using acetaldehyde instead of 4-carboxybenzaldehyde. Colorless oil, bp 97° C./18mm.

EXAMPLE 6

3-Benzyl-2,4-pentanedione

To a solution containing 5.5g of potassium tert-butoxide in 50ml of DMSO was added 6.0 g of 2,4-pentanedione followed by 5.0 g of benzyl chloride. The solution was stirred over night at room temperature. 200ml of 1 molar hydrochloric acid was added and the solution was extracted with dichloromethane. The extract was washed 3 times with water and the solvent was evaporated in vacuo. The residue was distilled. Yield 2.9 g, bp 150°–154° C./15 mm.

EXAMPLE 7

1,4-bis-(2-acetyl-3-oxo-1-butenyl)benzene

To a mixture containing 1.34 g of 1,4-benzenedicarboxaldehyde and 2.1 g of 2,4-pentanedione in 20ml of 2-propanol was gradually added 3.0 g of thionyl chloride with stirring and cooling below 20° C. The mixture was stirred over night at room temperature, filtered and washed with 2-propanol. Yield 1.1 g (55%).

EXAMPLE 8

3-Acetyl-4-(2-thienyl)-3-buten-2-one

The procedure described in example 1 was repeated by using thiophene-2-carboxaldehyde instead of 4-carboxybenzaldehyde. Yellowish oil, yield 70%.

EXAMPLE 9

3-Acetyl-4-(2-furyl)-3-buten-2-one

A solution containing 2.9g of furfural, 5.0 g of 2,4-pentanedione and 1 g of ammonium acetate in 25ml of 2-propanol was refluxed for 3 h. The solvent was evaporated in vacuo and the residue was purified by using column chromatography. Yellowish oil, yield 61%.

EXAMPLE 10

Dimethyl benzylidenemalonate

A mixture containing 10.6 g of benzaldehyde, 13.2 g of dimethylmalonate and 1 ml of ethyl-di(2-propyl)amine was heated over night at 120° C. The mixture was distilled in vacuo and the fraction boiling at 170°–180° C./18 mm was collected. Colorless oil, yield 1.9 g.

EXAMPLE 11

3-(3,4-Dihydroxybenzylidene)-2,4-pentanedione

The process described in example 1 was repeated by using 3,4-dihydroxybenzaldehyde instead of 4-carboxybenzaldehyde. Mp 134°–137° C.

EXAMPLE 12

3-Benzylidene-2,4-pentanedione

To a solution containing 6.3 g of 3-benzyl-2,4-pentanedione in 50 ml of dichloromethane was gradually added 5.3 g of bromine in 20 ml of dichloromethane under cooling (0°-5° C.). The solution was stirred for 10 min. at 0° C. and the solvent evaporated in vacuo. The residue was dissolved in 100 ml of pyridine and refluxed for 30 min. Pyridine was evaporated in vacuo, the residue was dissolved in dichloromethane and washed first with 6M hydrochloric acid and then with 2.6M NaOH. The solvent was evaporated and the residue distilled in vacuo. Bp 186°-188° C./16 mm, yield 1.2 g.

EXAMPLE 13

3-(2-Trifluoromethylbenzylidene)-2,4-pentanedione

To a solution of 2-trifluoromethylbenzaldehyde (8,7 g) and 2,4-pentanedione (5,01 g) in trifluoroacetic acid (10 ml) thionylchloride (4 ml) and catalytic amount of water (0,05 ml) were added at room temperature. The solution was stirred over night at 20°? C. The solvent was evaporated and the residue was distilled in vacuo, bp 110° C./1.5 mbar. Yield 5.3 g (41 %).

EXAMPLE 14

3-(4-Trifluoromethylbenzylidene)-2,4-pentanedione

4-Trifluoromethylbenzaldehyde (8,7 g) was condensed with 2,4-pentanedione (5,01 g) in a similar manner as described above. The crude product was crystallized from a mixture of ether-petroleum ether (1:1), mp 46°-48° C., yield 3.8 g (30%).

EXAMPLE 15

3-(3-Cyanobenzylidene)-2,4-pentanedione 3-cyanobenzaldehyde (2,62 g) was condensed with 2,4-pentanedione (3,0 g) in 2-propanol (10 ml) in the presence of ammonium acetate. Mp 63°-64° C., yield 1.27 g (30 %).

EXAMPLE 16

3-(4-Cyanobenzylidene)-2,4-pentanedione

4-Cyanobenzaldehyde (2.62 g) was condensed with 2,4-pentanedione (3.0 g) in 2-propanol (10 ml) in the presence of ammonium acetate. Mp 86°-88° C., yield 0.55 g (13 %).

EXAMPLE 17

3-(4-methoxybenzylidene)-2,4-pentanedione 4-methoxybenzyl chloride was condensed with 2,4-pentanedione as described in Example 6 to give 3-(4-methoxybenzyl)-2,4-pentanedione as an yellow oil. The crude product was treated first with bromine and then with pyridine as described in Example 12 to give the title compound, Mp 71°-72° C.

EXAMPLE 18

3-(4-Trifluoromethylbenzylidene)-2,4-pentanedione

The procedure described in Example 17 was repeated by using 4-trifluoromethylbenzyl chloride. mp 46°-47° C.

EXAMPLE 19

3-(4-Cyanobenzylidene)-2,4-pentanedione

The procedure described in Example 17 was repeated by using 4-cyanobenzyl chloride. mp 86°-88° C.

EXAMPLE 20

3-Acetyl-4-(2-thienyl)-3-buten-2-one

The procedure described in Example 17 was repeated by using 2-choloromethylthiophene. Yellow oil.

EXAMPLE 21

3-Acetyl-4-(2-furyl)-3-buten-2-one

The procedure described in Example 17 was repeated by using 2-chloromethylfuran. Yellow oil.

EXAMPLE 22

3-(4-Carboxybenzylidene)-2,4-pentanedione

The procedure described in Example 17 was repeated by using methyl 4-chloromethylbenzoate to give 3-(4-methoxycarbonyl-benzylidene)-2,4-pentanedione as an yellow oil. The crude product was hydrolyzed with diluted sodium hydroxide solution and acidified with hydrochloric acid to give the title compound, mp 196°-199° C.

EFFECT OF SUBSTITUTED βDIKETONES IN VIVO

Oral administration of absolute ethanol to rats results in severe gastric damage consisting of grossly hemorrhagic and necrotic lesions. Compounds which are able to prevent the ethanol-induced lesions are called cytoprotective 6r gastroprotective agents.

Male Wistar rats were orally dosed (5 ml/kg) with a test compound suspended in 5% gum arabic. Control animals received pure vehicle. Half an hour later the rats were orally administered with 1 ml of absolute ethanol. The animals were sacrificed one hour after ethanol administration and the total area of macroscopic lesions in each stomach was calculated in $mm^2$. The extent of duodenal damage was measured in cm from pylorus.

The results are summarized in table 1.

TABLE 1

The effect of some substituted β-diketones on the area of ethanol-induced gastric damage in rats. The mean area of lesions in control rats was 79.8 ± 8 $mm^2$ and the extent of damage in duodenum 4 ± 1 cm (n = 39).

| Example No. | Compound No. 1) | Dose mg/kg p.o. | Reduction in lesion area % (ventricle) | Reduction in lesion length % (duodenum) |
|---|---|---|---|---|
| 2 | 1 | 3 | 72 | — |
|   |   | 10 | 55 | 63 |
|   |   | 30 | 96 | 99 |
|   |   | 100 | 98 | 97 |
| 3 | 2 | 3 | 66 | — |
|   |   | 10 | 86 | — |
|   |   | 100 | 100 | 64 |
| 4 | 3 | 50 | 96 | 86 |
| 5 | 4 | 50 | 92 | 86 |
| 6 | 5 | 50 | 79 | 66 |
| 10 | 6 | 100 | 72 | 78 |
| 11 | 7 | 100 | 67 | 89 |
| 8 | 8 | 75 | 99 | 97 |
| 9 | 9 | 75 | 95 | 97 |
| 1 | 10 | 100 | 96 | 81 |
| 7 | 11 | 100 | 67 | 51 |
| Compound of UK | 12 | 3 | 42 | 5 |
|   |   | 30 | 67 | 79 |

TABLE 1-continued

The effect of some substituted β-diketones on the area of ethanol-induced gastric damage in rats. The mean area of lesions in control rats was 79.8 ± 8 mm² and the extent of damage in duodenum 4 ± 1 cm (n = 39).

| Example No. | Compound No. 1) | Dose mg/kg p.o. | Reduction in lesion area % (ventricle) | Reduction in lesion length % (duodenum) |
|---|---|---|---|---|
| Pat. No. 8730190 | | 100 | 96 | 70 |
| 13 | 13 | 10 | 79 | 7 |
| 14 | 14 | 3 | 69 | 45 |
|    |    | 10 | 79 | 37 |
| 15 | 15 | 3 | 76 | |
|    |    | 10 | 88 | 25 |
|    |    | 30 | 100 | 96 |
| 16 | 16 | 3 | 55 | |
|    |    | 10 | 95 | 81 |
|    |    | 30 | 97 | 99 |

1)The chemical names of the compounds are listed on the next page.
1)Compound
1 = 3-(4-hydroxybenzylidene)-2,4-pentanedione
2 = 3-(4-methoxybenzylidene)-2,4-pentanedione
3 = 3-(benzylidene)-2,4-pentanedione
4 = 3-ethylidene-2,4-pentanedione
5 = 3-benzyl-2,4-pentanedione
6 = dimethyl benzylidenemalonate
7 = 3-(3,4-dihydroxybenzylidene)-2,4-pentanedione
8 = 3-acetyl-4-(2-thienyl)-3-buten-2-one
9 = 3-acetyl-4-(2-furyl)-3-buten-2-one
10 = 3-(4-carboxybenzylidene)-2,4-pentanedione
11 = 1,4-bis-(2-acetyl-3-oxo-1-butenyl)benzene
12 = 3-(3,4-dihydroxy-5-nitrobenzylidene)-2,4-pentanedione, the reference compound
13 = 3-(2-trifluoromethylbenzylidene)-2,4-pentanedione
14 = 3-(4-trifluoromethylbenzylidene)-2,4-pentanedione
15 = 3-(3-cyanobenzylidene)-2,4-pentanedione
16 = 3-(4-cyanobenzylidene)-2,4-pentanedione All the substituted β-diketones significantly reduce the ethanol-induced mucosal lesions in the stomach, and this reduction is dependent on the dose administered. Moreover, the damage area of the duodenum was smaller and less severe in animals treated with the present compounds than in the control animals. It can therefore be seen that the present compound gave gastroprotective activity both in the stomach and in the duodenum.

We claim:

1. A compound of the formula Ib:

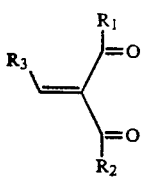

wherein $R_1$ and $R_2$ are independently $C_{1-6}$ alkyl which is unsibstituted or substituted by hydroxy, $C_{1-6}$ alkoxy, halogen, nitro or amine, $C_{1-6}$ alkoxy, phenyl or naphthyl which are unsibstituted or substituted by $C_{1-6}$ alkyl, hydroxy, $C_{1-6}$ alkoxy, halogen, nitro amine or carboxy or one of the following heteroaryl groups: pyridyl, quinolyl, thienyl or furyl which are unsubstituted or substituted by $C_{1-6}$ alkyl, hydroxy, $C_{1-6}$ alkoxy, halogen, nitro or amine; $R_3$ is $C_{1-6}$ alkyl which is substituted by hydroxy, $C_{1-6}$ alkoxy, halogen, nitro or amine, phenyl or naphthyl which are substituted by trifluoromethyl, cyano, or one of the following heteroaryl groups: quinolyl, thienyl or furyl which are substituted by hydroxy, $C_{1-6}$ alkoxy, halogen, nitro or amine or a salt thereof, provided that when $R_3$ is substituted furyl it is not substituted by halogen or nitro and if $R_3$ is a phenyl which is substituted by cyano then the cyano is not in the para position.

2. A compound according to claim 1 in which $R_1$ and $R_2$ are each $C_{1-4}$ alkyl.

3. A compound according to claim 1 where the compound is 3-(2-trifluoromethylbenzylidene)-2,4pentanedione.

4. A compound according to claim 1 where the compound is 3-(4-trifluoromethylbenzylidene)-2,4pentanedione.

5. A compound according to claim 1 where the compound is 3-(3-cyanobenzylidene)-2,4pentanedione.

6. A pharmaceutical composition comprising an effective amount of a compound according to formula Ib:

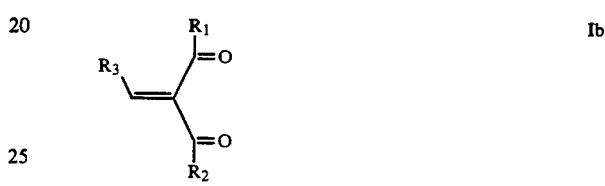

wherein $R_1$ and $R_2$ are independently $C_{1-6}$ alkyl which is unsubstituted or substituted by hydroxy, $C_{1-6}$ alkoxy, halogen, nitro or amine, $C_{1-6}$ alkoxy, phenyl or naphthyl which are unsubstituted or substituted by $C_{1-6}$ alkyl, hydroxy, $C_{1-6}$ alkoxy, halogen, nitro, amine or carboxy or one of the following heteroaryl groups: pyridyl, quinolyl, thienyl or furyl which are unsubstituted or substituted by $C_{1-6}$ alkyl, hydroxy, $C_{1-6}$ alkoxy, halogen, nitro or amine; $R_3$ is $C_{1-6}$ alkyl which is substituted by hydroxy, $C_{1-6}$ alkoxy, halogen, nitro or amine, phenyl or naphthyl which are substituted by trifluoromethyl, cyano, or one of the following heteroaryl groups: quinolyl, thienyl or furyl which are substituted by hydroxy, $C_{1-6}$ alkoxy, halogen, nitro or amine or a salt thereof, provided that when $R_3$ is substituted furyl it is not substituted by halogen or nitro and if $R_3$ is a phenyl which is substituted by cyano then the cyano is not in the para position, to treat or prevent ulcers, lesions or like conditions in the gastrointestinal tract, and a pharmaceutically acceptable carrier or diluent.

7. A pharmaceutical composition according to claim 6 where $R_1$ and $R_2$ are $C_{1-4}$ alkyl and $R_3$ is thienyl, furyl or phenyl which is substituted by trifluoromethyl or cyano.

8. A pharmaceutical composition according to claim 6 where the compound according to formula Ib is selected from the group consisting of 3-(4-methoxybenzylidene)-2,4-pentanedione, 3-ethylidene-2,4-pentanedione, dimethyl benzylidenemalonate, 3-acetyl-4-(2-furyl)-3-buten-2-one, 3-acetyl-4-(2-thienyl)-3-buten-2-one, 1,4-bis-(2-acetyl-3-oxo-1-butenyl)benzene, and 3-(2-trifluoromethylbenzylidene)-2,4-pentanedione.

9. A method of prophylaxis or treatment of ulcers, lesions or like conditions in the gastrointestinal tract comprising administering an effective amount of a compound according to formula Ib

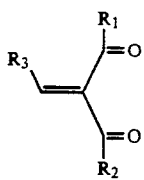

wherein $R_1$ and $R_2$ are independently $C_{1-6}$ alkyl which is unsubstituted or substituted by hydroxy, $C_{1-6}$ alkoxy, halogen, nitro or amine, $C_{1-6}$ alkoxy, phenyl or naphthyl which are unsubstituted or substituted by $C_{1-6}$ alkyl, hydroxy, $C_{1-6}$ alkoxy, halogen, nitro, amine or carboxy or one of the following heteroaryl groups: quinolyl, thienyl or furyl which are unsubstituted or substituted by $C_{1-6}$ alkyl, hydroxy, $C_{1-6}$ alkoxy, halogen, nitro or amine; $R_3$ is $C_{1-6}$ alkyl which is unsubstituted or substituted by hydroxy, $C_{1-6}$ alkoxy, halogen, nitro or amine, a phenyl or naphthyl which are unsubstituted or substituted by $C_{1-6}$ alkyl, $C_{1-6}$ alkoxy, trifluoromethyl, cyano, amine or carboxy or a diketo group attached to the aryl group directly or via a saturated hydrocarbon chain of 1 to 3 carbon atoms or an unsaturated hydrocarbon chain of 2 or 3 carbon atoms; or one of the following heteroaryl groups: pyridyl, quinolyl, thienyl or furyl which are unsubstituted or substituted by $C_{1-6}$ alkyl, hydroxy, $C_{1-6}$ alkoxy, halogen, nitro or amino or a salt thereof to a patient in need of such prophylaxis or treatment; with the proviso that if $R_3$ is phenyl, then the phenyl group can have only one or two substituents.

10. A method according to claim 9 where the compound according to formula Ib is selected from the group consisting of 3-benzylidene-2,4-pentanedione, 3-(4-methoxybenzylidene)-2,4-pentanedione, 3-ethylidene-2,4-pentanedione, dimethyl benzylidenemalonate, 3-acetyl-4-(2-furyl)-3-buten-2-one, 3-acetyl-4-(2-thienyl)-3-buten-2-one, 3-(4-carboxybenzylidene)-2,4-pentanedione, 1,4-bis-(2-acetyl-3-oxo-1-butenyl)benzene, 3-(2-trifluoromethylbenzylidene)-2,4-pentanedione and 3-(4-cyanobenzylidene)-2,4-pentanedione.

* * * * *